United States Patent [19]

Feldmann

[11] 4,159,649
[45] Jul. 3, 1979

[54] APPARATUS FOR THE GENERATION OF SPECIFIED DEFORMATIONS IN SPECIMEN

[76] Inventor: Eckard Feldmann, Feldstedter Weg 6, D 1 Berlin 49, Fed. Rep. of Germany

[21] Appl. No.: 813,752

[22] Filed: Oct. 31, 1977

[30] Foreign Application Priority Data

Oct. 8, 1976 [DE] Fed. Rep. of Germany ....... 2645474

[51] Int. Cl.² .............................................. G01N 3/08
[52] U.S. Cl. .................................................... 73/788
[58] Field of Search .................... 73/101, 94, 95, 788, 73/818

[56] References Cited

U.S. PATENT DOCUMENTS

3,416,363  12/1968  Siems .................................. 73/101 X
3,939,701  2/1976  Peschl ................................... 73/101

Primary Examiner—Jerry W. Myracle

[57] ABSTRACT

Technique for the generation of stretchings, simple shear, and other definite deformations in a specimen. The deformation is generated by help of mechanical means by impressing definite displacements to the particles located on the surface of the specimen. The mechanical means are plates, bars, and rods underlying restrictions with respect to motion, so that by relative displacement of these elements the definite displacements required are obtained.

8 Claims, 25 Drawing Figures

APPARATUS FOR THE GENERATION OF SPECIFIED DEFORMATIONS IN SPECIMEN

CROSS-REFERENCES TO RELATED APPLICATIONS

There are other methods for the generation of definite deformations in materials, like certain test methods in soil mechanics. But none of these uses the method presented herein.

BACKGROUND OF THE INVENTION (1) Field of the Invention

One field of application of this invention is the testing and measuring of functional relations between stress and deformation in materials, possibly in dependence of parameters like temperature and aging. In particular, the necessity for the generation of homogeneous deformations is fundamental in the theory of the strength of materials and is the basis for the determination of parameters in constitutive equations, e.g. the modulus of elasticity or viscosity.

A class of homogeneous deformations that is generable by the apparatus described herein is specified by the equations of motion $x = cX + ky$, $y = aY$, $z = bZ$ in a rectilinear basis with small letters indicating coordinates of particles in a deformed, big letters indicating those in a reference configuration. The coefficient functions a, b, c, k are dependent of time. For $a = b = c = 1$, the deformation is called 'simple shear', for $k = 0$ we have the case of stretching.

Another field of application is that of technological tests. Their purpose is the searching of the strength of materials under deformation processes similar to those occuring in some construction of interest.

(2) Description of the Prior Art

Concerning the method, there is no prior art known to the inventor. The necessity for the generation of definite homogeneous deformations is well-known: The Non-Linear Field Theories of Mechanics, *Encyclopedia of Physics*, Volume III/3, Springer Verlag, N.Y. 1965, page 179.

SUMMARY

The patent is claimed for a class of devices by which definite deformations, in particular homogeneous deformations, in a specimen consisting of some material can be generated by impressing definite displacements to surface elements. These are generated by relative displacement of elements called plates, bars, and rods. The invention concerns the kinematical function of the different elements in order to generate definite displacements in points on the surface of a specimen to be tested. The kinematical functions are explained in detail in connection with the embodiments.

The advantages going along with the application of apparatus according to this invention are: Auxiliary fields of displacement can be generated, for example such as are needed for the research of the response of materials in construction. For technical purposes the method is accurate. For most problems of the generation of definite deformations there are no devices known more simple than those described herein, though there are no existing models for comparison.

DESCRIPTION OF THE PREFERRED EMBODIMENTS

Detailed Description

Figure 1:
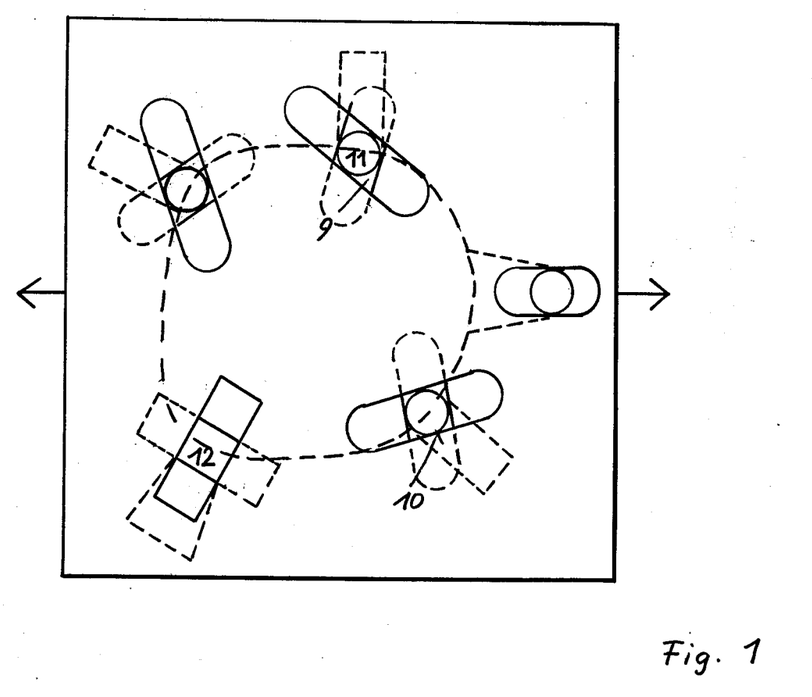
FIGS. 1 and 2: There are two pairs of plates (1), (2) and (3), (4). The plates of both pairs belong either to one or the other of two classes. Through the crossection of slots, bars are inserted enclosing a cylindrical specimen (7). The deformation is impressed as is indicated by vectors.
Figure 2:
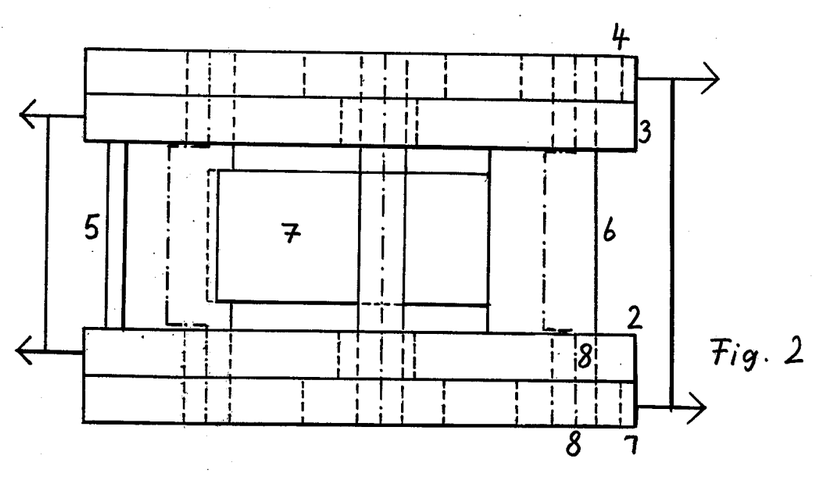

FIGS. 1 and 2 depict two pairs of plates, (1), (2) and (3), (4), one plate of each pair belonging to a different class, and the plates having surfaces parallel or almost parallel to each other. The plates have the same number of slots and the slots belonging to different classes of plates correspond to each other one to one. This correspondence is characterized by two facts. Projected onto a third plane, usually, the axes of corresponding slots are not collinear, so that when projected, the slots intersect. The bars (5), (6) are put through the intersection of slots (9). The number of bars is the same as is the number of slots belonging to one plate. The crossection of the bar in the region of the slots may be identical with the crossection of slots in their projection (12), or, the bar may touch the surfaces of the slots, (11). The bars are placed in a more or less regular sequence around the specimen. The displacement of the bars when displacing the plates is impressed to the surface of the specimen (7). In order to enable measurement of forces acting in and on the surface of the specimen and in order to make rapid exchange of the specimen possible, further elements may be arranged between surface and bars. The axis of the bar in the region of crossecting slots must be collinear with a line lying in the surface of the specimen and should be able to rotate around it if forces not normal to the surface of the specimen occur, (5). This is the case, if the specimen is deformed nonsymmetrically relative to the bar. In case normal forces occur exclusively on the surface of the specimen, the axis in the region of slots need not be collinear with a line in the surface of the specimen, (6). Beyond that, the axis of bars may be auxiliary. It even may have right angles, (5), (6). The specimen may have cylindrical, (7), or prismatic shape. The crossection of the specimen parallel to the surfaces of the plates may be a square, a circle, or something else. Usually, in applications the axis of a slot is a straight line. However, sometimes the axis may be nonlinear. It is needed for the generation of deformations of constant deformation gradient of second order or some different definite deformation. The bars may be placed on metals especially suited for gliding under high pressure. These may be metals containing graphite, oil, or some other material for the reduction of roughness.

Figure 3:
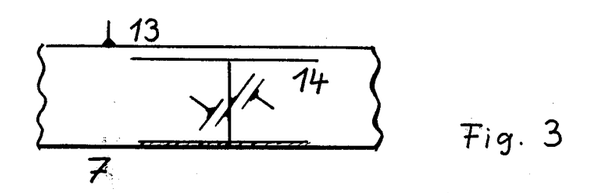
FIG. 3: Schematic representation of a detail of the function according to claim 2. The bar (14) is attached to the specimen (7) and displaceable relative to the element (13) and slots in elements (15) which are parallel to the drawing plane. Slots are symbolized by ||.
Figure 4:
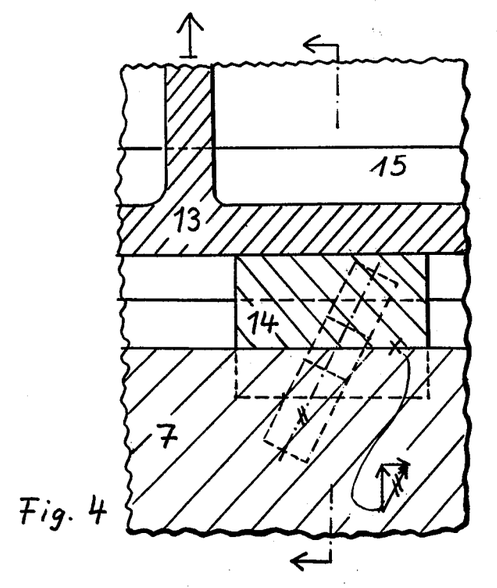
FIGS. 4 and 5 depict the embodiment of the principle according to FIG. 3. Vectors represent the motion of the different elements.
Figure 5:
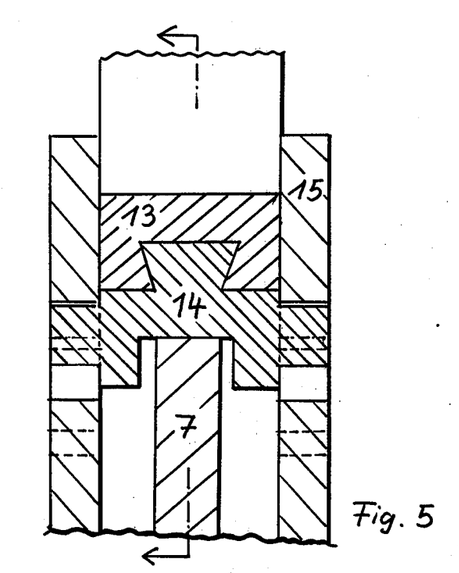
Figure 6:
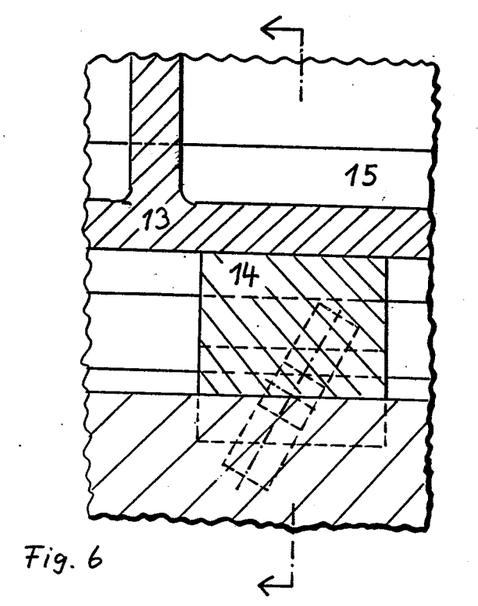
FIGS. 6 and 7 are closely related to the FIGS. 4 and 5: The first device represented is good for the generation of plane stress in a specimen, the second is suited for the generation of plane strain because of the additional plates (19) restricting the deformation of the specimen (7).
Figure 7:
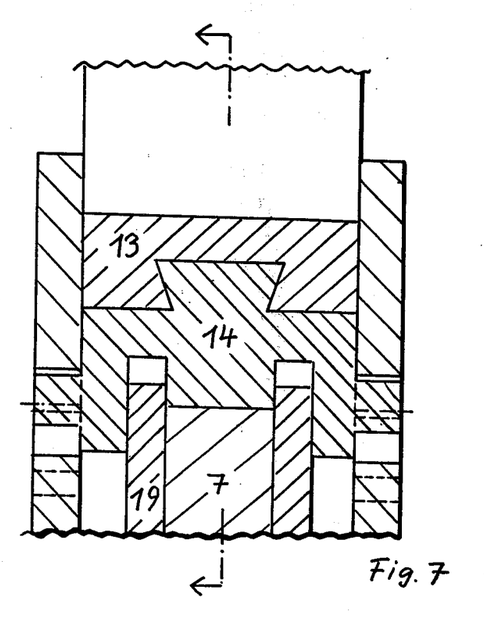
Figure 8:
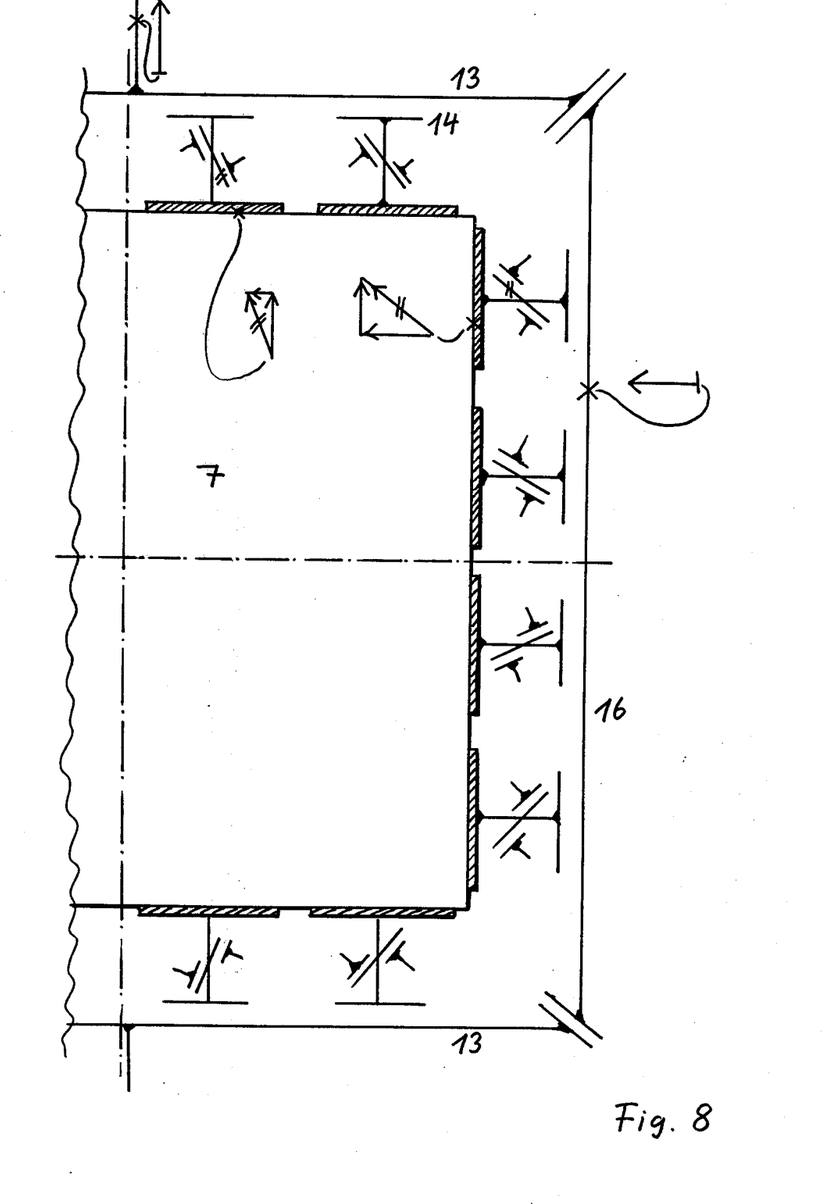
FIG. 8 is the schematic representation of one half of symmetric devices according to claim 2. One detail was already represented by FIGS. 3 to 7.
Figure 9:
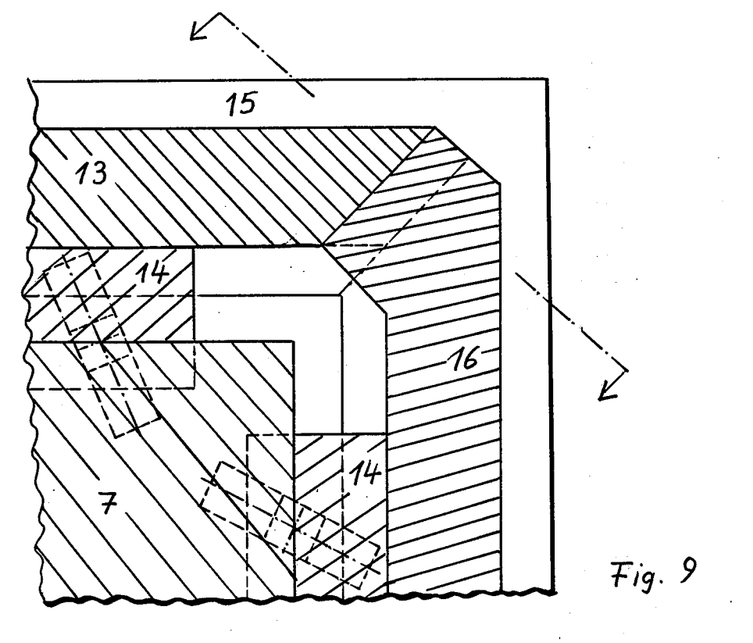
FIGS. 9 and 10: The detail of the embodiment of the connection of parts (13) and (16) is depicted.
Figure 10:
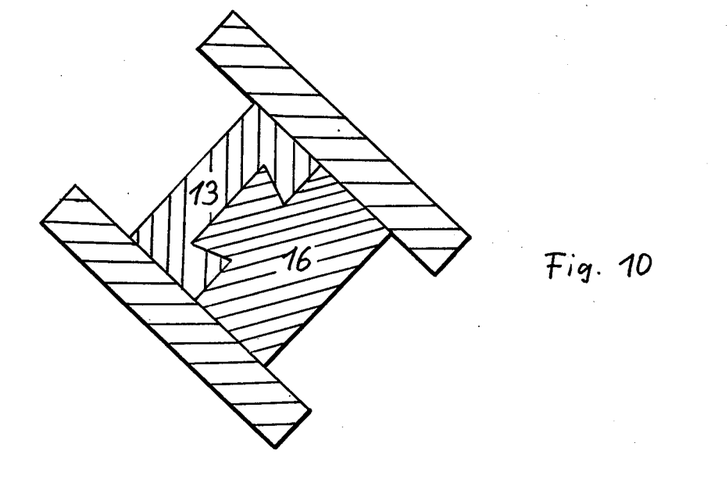
Figure 11:
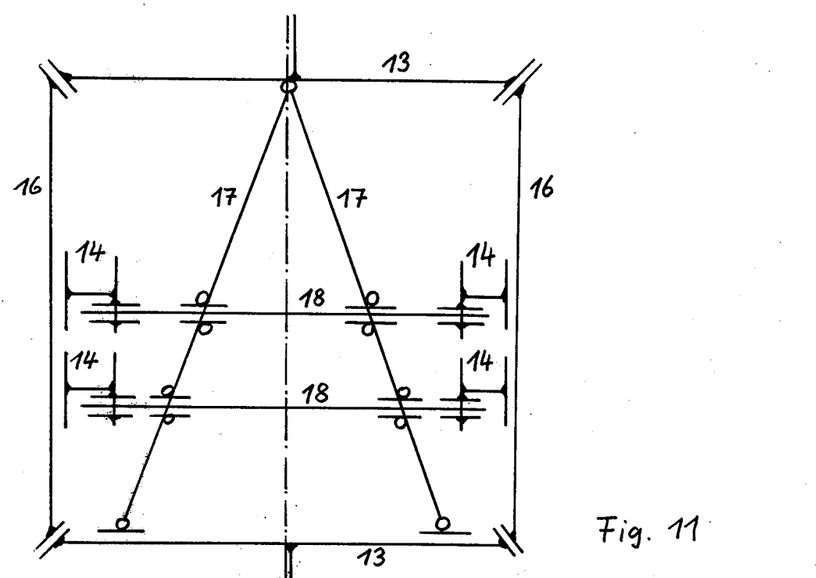
FIG. 11: Schematic representation of the function of devices according to claim 3. Bars and plates are represented by lines, hinges by o, and movable bearings by symbols ||.
Figure 12:
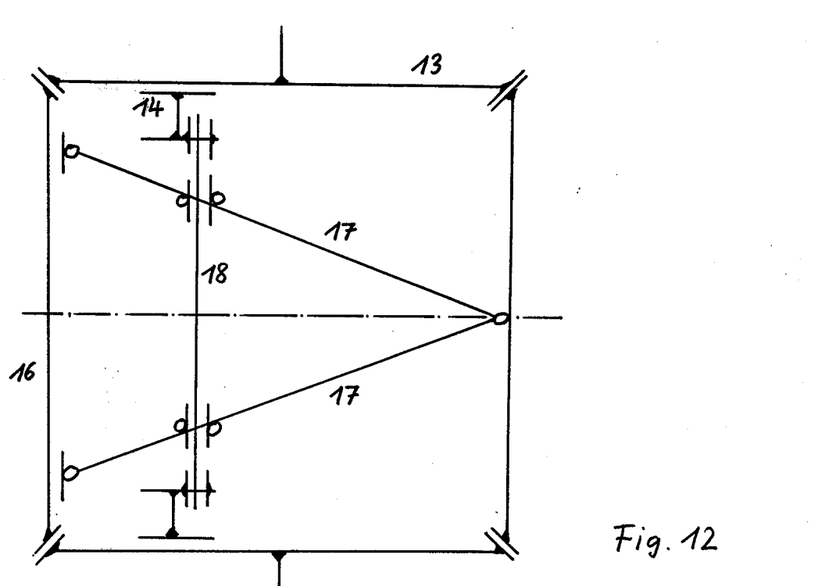
FIG. 12: The same as is represented in FIG. 11, but bars (17) and (18) have been rotated by a right angle. Both representations may be superposed. The displacement is impressed to the elements (13).
Figure 13:
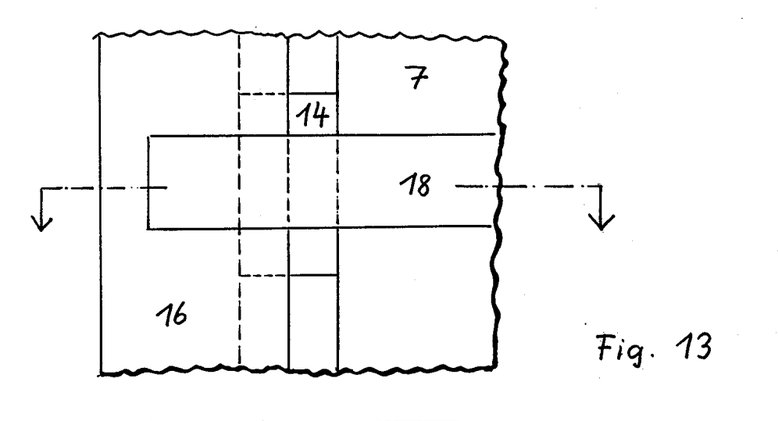
FIGS. 13 and 14: Representation of an embodiment of a detail from FIG. 11.
Figure 14:
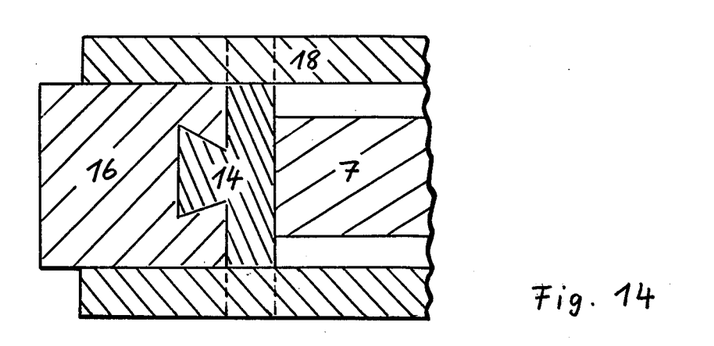
Figure 15:
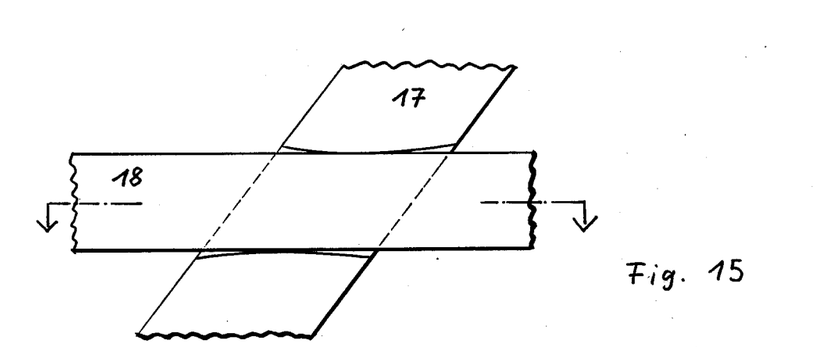
FIGS. 15 and 16: Representation of another embodiment from FIG. 11.
Figure 16:
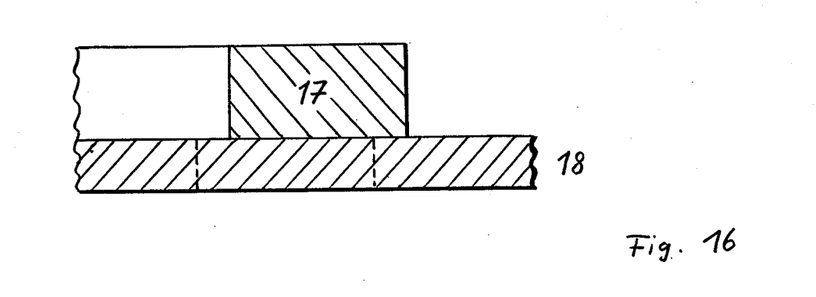
Figure 17:
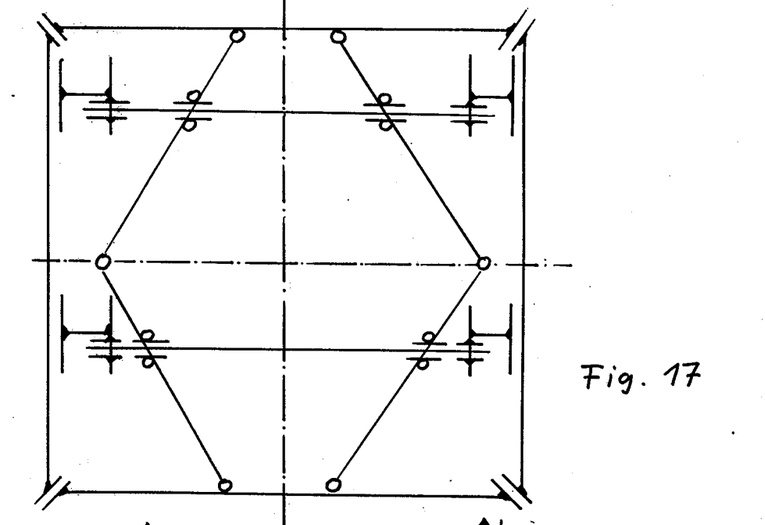
FIG. 17: Schematic representation of the function of devices according to claim 4.
Figure 18:
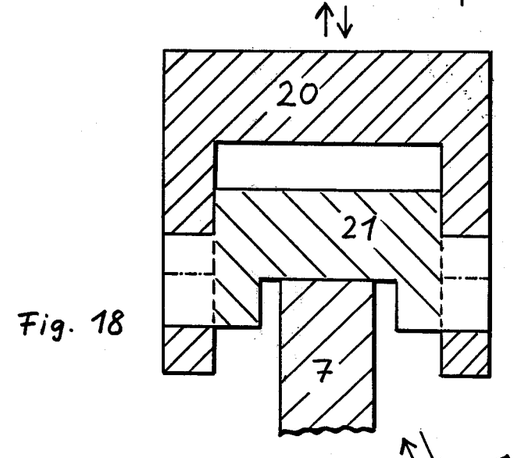
FIGS. 18 and 19: Representation of the embodiment of the function according to claim 5. The bar (21) being attached to the specimen (7) is supported by the frame (20).
Figure 19:
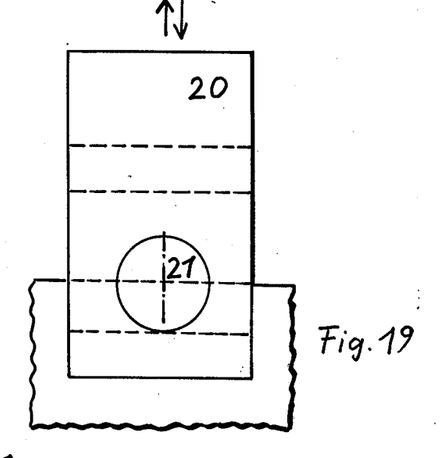
Figure 20:
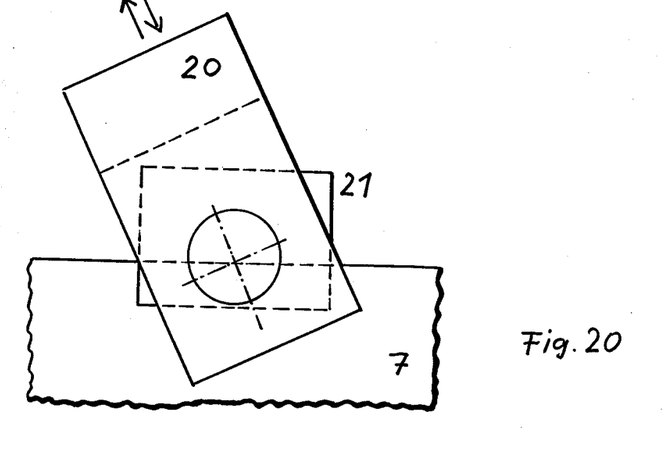
FIG. 20 is different from FIG. 19 in that the frame has been rotated. Vectors indicate displacements.
Figure 21:
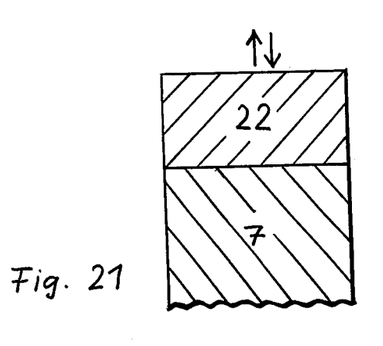
FIGS. 21 and 22: Side view and crossection of the embodiment of the function of the device according to claim 6.
Figure 22:
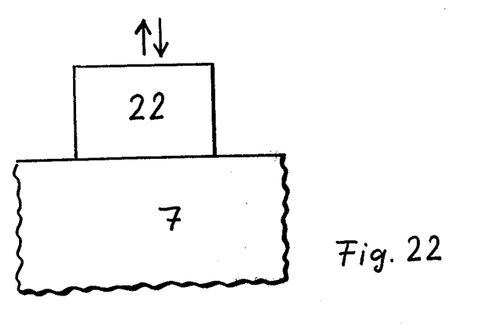
Figure 23:
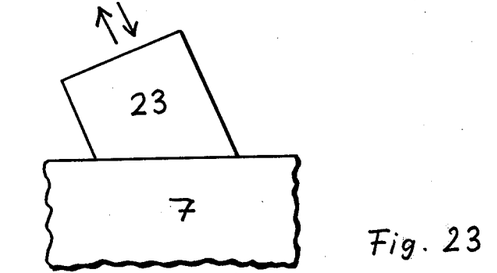
FIG. 23 differs from FIGS. 21 and 22 in the placement of the bars (22) and (23), respectively.

The device can be given a specialization if specimen with plane surfaces are used, in particular specimen of cubic shape. According to the description given above, the definite displacement of a point was generated by the displacement of the point lying in the intersection of the axes of corresponding slots. By the restriction that the surface is a plane, the one component of the displacement can be generated by the motion of a plate, elements (13) and (16), FIG. 8, which is parallel to the surface of the specimen. The displacement is impressed to the surface of the specimen by elements (14) located between the plates (13) and (16), respectively, and the surface and are fixed orthogonally to both, surface and plate. But their displacement in directions lying in the surface, so far, is not restricted. This is symbolized by lines parallel to each other, ||. The other component of the displacement is generated the way already described: the ends of the elements (14) are placed in slots of the plates (15) which are orthogonal to the plates (13) and (16). The position of the plate can either be thought fixed in space or fixed relative to some system exhibiting properties of symmetry, or fixed relative to one of the plates (13). Accordingly, the geometry of the slots in order to generate some definite deformation depends thereon. In FIG. 3, this is represented symbolically. In FIG. 4 an example is given. Displacements are symbolized by vectors. The restriction of strain in the direction orthogonal to the plates (15) can be obtained by two plates (19), FIGS. 6 and 7, placed between the plates (15) and the surfaces of the specimen and contacting the surface. The plates (19) can be fixed relative to one another in the direction normal to the surface of the specimen by placing them in slots of elements (14). If the surfaces of the specimen neither contact plates (19) nor plates (15), we have the case of plane stress. The motion of the plates (13) and (16) is usually determined by a relation between them. If this relation is a linear one, it is best to realize this relation by mechanical means. It is done by movable bearings that allow displacements in one direction only. The direction lies in a plane that is parallel to the plate (15). The direction of the displacement depends on the relation to be realized. For example, the motion of some points of the plates (13) and (16) and some points of the specimen are depicted in FIG. 8. By FIGS. 9 and 10, one possible construction is given. Instead of plates (15), use can be made of rods connecting plates (13) and (16), respectively. To them, rods (18) are attached which serve to impress the relative displacement of plates (13) and (16), respectively, to the elements (14) attached to plates (16) and (13), respectively. The value of the displacement impressed is linear in proportion relative to the location of plates (13) and (16), respectively. Two examples are given by FIGS. 11 and 12. They can be superposed. A construction for a movable bearing is depicted in FIGS. 13 and 14. The symbol of the small circle represents a hinge with an axis orthogonal to the drawing plane. The number of elements (18) depends on the requirements for homogeneity in regions near the surface of the specimen. For most technical purposes 5 to 8 for each surface may be sufficient. In order to avoid the construction of the movable hinge, one can make use of a construction depicted in FIG. 17 and characterized by claim 4. The rods, too, can be arranged between plates (16). Both can be superposed.

By the claims 5, 6, 7, and 8 devices are characterized that have in common that the displacement to be impressed to a point of the surface of the specimen may be generated by hydraulics. Since, besides properties of symmetry, these displacements are independent of each other, the necessity arises to generate each displacement independently of others. This can be done by an electronic, automatic control device. In FIGS. 18–23 possible displacements are symbolized by vectors. Since the vector of displacement need not maintain its direction during deformation, the bar (21) may rotate relative to the frame (20), by which the bar is supported. The displacement to be impressed to the surface of the specimen is impressed to the frame (20). Furthermore, this kind of bearing has the advantage that in case of large deformations, rotations of the surface relative to the direction of the impressed displacement will cause no stress. The axis of the bar (21) in the region of the bolts, which are supported by the frame, should be collinear with a line in the surface of the specimen.

Figure 24:
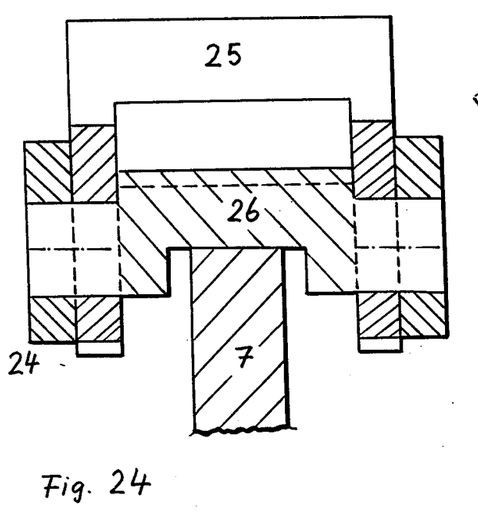
FIGS. 24 and 25: Representations of the embodiment of the function according to claim 7. The bar (21) being attached to the specimen (7) is supported by frames (24) and (25).
Figure 25:
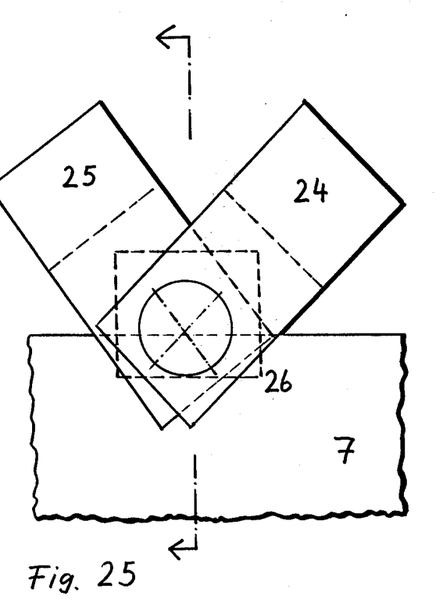

For small deformations and deformations that have to be generated for the comparison of the behavior of similar materials, it may be preferable and sufficient to impress displacements by single elements (22), which may be plates or bars. The elements (21) and (22), respectively, are attached to the surface of the specimen e.g. by an adhesive material as needed. This depends on the kind of forces and roughness of the surfaces. The relation between deformations occuring in different directions of one specimen may be a linear one over time. This is a special but important case. Sometimes, the necessity arises to impress to the different points of the surface of the specimen displacements which are not related to each other. Then, in the two dimensional case, two components, in the three dimensional case, three components of the displacement have to be impressed to the point independently. This means that in the plane case instead of one, two frames (24) and (25), by which the bar is supported, have to be used. In the three dimensional case three frames or functionally equivalent elements have to be used. The axes of hinges and joints should be collinear with lines in the surface of the specimen. In case of small deformations the frames may be replaced by rods, possibly subdivided by hinges or joints. If they are present, they should be located to the surface of the specimen as near as possible. This is valid in particular for the axes of hinges and joints.

Preferred embodiments are the following: In order to generate some definite deformation, there is no kinematical principle more simple than that specified by claim 1. The linear displacement of the two classes of plates is directly transformed into a manifold of different displacements, which are impressed to the surface of the specimen. The construction is suited best for the testing of specimen of cylindrical shape. The second construction, specified by claim 2, is the most simple one for the generation of definite deformations in cubical specimen of greater strength. This is because the contact force between the bolts at the ends of the elements (14) and the sufaces of the slots of the plates (15) may be greater than the corresponding forces occuring in the first construction. The applicability of the second construction is not covered by the first one. The advantage of the construction specified by the claims 3 and 4 depends on the fact that by a great number of elements (18) a better homogeneity of the deformation can be obtained in regions near the surface of the specimen than can be reached by the constructions specified by the claims 1 and 2, since for them it is difficult to have a greater number of slots. The advantage of the constructions specified by the claims 5 and 7 in comparison with the ones described before is that for different deformations of the specimen the same device may be applied. But it is more expensive than the devices based on mechanical principles exclusively. It is therefore preferable for nostandard tests. Beyond that, for periodic deformations the abrasion may cause problems with devices based on mechanical functions; with devices based on claims 5 to 8 this poses no problem. In case of small deformations, devices specified by claims 5 and 7 equate with the devices specified by claims 6 and 8.

Preferred embodiments valid for all examples given are the following: The specimen is cubical, cylindrical, or prismatic. The number of bars (5) and (6), respectively, is 8, the number of elements (14) belonging to one surface is 5, the number of elements (18) is 10. The number of elements (21), (22), (23), and (26) depends on the strength of the material to be tested and the size of the deformation required. The range varies from 8 to 48.

What is claimed is:

1. Apparatus for the generation of definite homogeneous and nonhomogeneous deformations in a specimen, the apparatus consisting of bars and plates having parallel bordered slots, characterized by two pairs of plates, each of the plates of one pair belonging to a different class, the two classes differing by the geometry of slots, the plates being parallel to each other, slots belonging to different classes of plates corresponding one to one and intersecting in the projection onto a plane parallel to the plates, bars put through the intersection of corresponding slots, the bars being attached to the specimen, having an axis in the region of slots being collinear with a line in the surface of the specimen if the specimen is deformed nonsymmetrically relative to the bar, the operation of the device results in a definite deformation of the specimen if the plates of the two classes are displaced relative to each other.

2. Apparatus consisting of bars and plates, characterized by two plates (15) parallel to each other and parallel to two different surfaces of a cubical specimen, the plates having parallel bordered slots of identical geometry into which bars (14) are put, the bars being attached to the specimen and having an axis in the region of the slots which is collinear with a line in the surface of the specimen if the specimen is deformed nonsymmetrically relative to the bar, by plates (13) and (16) being orthogonal to each other and orthogonal to the plates (15), being parallel to the surfaces of the specimen, placed opposite to each other, and displaceable relative to each other in directions lying in the same plane parallel to the plates (15), by the bars (14) being arranged between plates (13) and (16), respectively, and the surface of the specimen, and, in displacement, moving parallel exclusively relative to the plates (13) and (16), respectively, the operation of the device results in a definite deformation of the specimen if the plates (13) are displaced relative to each other.

3. Device as defined in claim 2, characterized by the deletion of plates (15) from the device, by rods (17) being attached to the plates (13) and (16), respectively, by hinges, by one of the hinges of each rod (17) being movable in a direction which is parallel to the plates (13) and (16), respectively, by the rods (17) being arranged symmetrically relative to the axis of symmetry which is orthogonal to the plates (13) and (16), respectively, by rods (18) being attached to the rods (17) and elements (14) by movable bearings which confine the movement of the rods (18) in the direction of their axis, the operation of the device results in a definite deformation of the specimen if the plates (13) are displaced relative to each other.

4. Device as defined in claim 3, characterized by hinges having an axis orthogonal to the drawing plane dividing rods (17) which are attached to the plates (13) and (16) respectively by hinges.

5. Device consisting of displacement means, frames, and bars, characterized by bars (21) enclosing a specimen, carrying at the bars' ends bolts hinged in a frame, the bars (21) being attached to the specimen, the number of bars and frames being at least 2 for each plane of specimen with plane surface, and the number of bars and frames enclosing the specimen being at least 5, the operation of the device results in a definite deformation of the specimen if definite displacements are impressed to the frames by the displacement means.

6. Device as defined in claim 5, which is characterized by two frames (24) and (25) per bar instead of one per bar.

7. Device consisting of displacement means and bars enclosing a specimen and being attached to it, the number of bars being at least 2 for each plane of specimen with plane surface, the number of bars enclosing the specimen being at least 5, the operation of the device results in a definite deformation of the specimen if definite displacements are impressed to the bars by the displacement means.

8. Device consisting of displacement means, rods, and plates, characterized by plates enclosing a specimen and being attached to it, by rods attached to the plates by a hinge in the two dimensional case and a spherical joint in the three dimensional case, respectively, the number of rods per plate being 2 in the two dimensional case, the number of rods per plate being 3 in the three dimensional case, the operation of the device results in a definite deformation of the specimen if definite displacements are impressed to the rods by the displacement means.

* * * * *